United States Patent [19]

Mon

[11] Patent Number: 4,644,781

[45] Date of Patent: Feb. 24, 1987

[54] FLUID PROPERTY MEASURING DEVICE

[75] Inventor: George Mon, Silver Spring, Md.

[73] Assignee: The United States of America as represented by the Secretary of the Army, Washington, D.C.

[21] Appl. No.: 679,343

[22] Filed: Dec. 7, 1984

[51] Int. Cl.⁴ .......................................... G01N 11/04
[52] U.S. Cl. .................................... 73/55; 73/861.19; 73/54; 137/820
[58] Field of Search .............. 73/861.19, 55, 54, 32 R; 137/820

[56] References Cited

U.S. PATENT DOCUMENTS

| | | | |
|---|---|---|---|
| 2,934,944 | 5/1960 | Eolkin | 73/55 |
| 3,138,950 | 6/1964 | Welty et al. | 73/55 |
| 3,392,630 | 7/1968 | Schultz | 73/55 |
| 3,443,574 | 5/1969 | Posingies | 137/820 |
| 3,461,896 | 8/1969 | Holloway | 137/820 |
| 3,543,782 | 12/1970 | Bauer | 137/820 |
| 3,590,840 | 7/1971 | Hyer | 137/820 |
| 3,605,778 | 9/1971 | Metzger | 73/861.19 |
| 3,610,026 | 10/1971 | Topham | 73/55 |
| 3,695,283 | 10/1972 | Ringwall | 137/820 |
| 3,986,527 | 10/1976 | Mon | 137/819 |
| 4,384,472 | 5/1983 | Tournier | 73/55 |
| 4,425,790 | 1/1984 | Bice et al. | 73/55 |

FOREIGN PATENT DOCUMENTS

| | | | |
|---|---|---|---|
| 641322 | 1/1979 | U.S.S.R. | 73/55 |
| 669268 | 6/1979 | U.S.S.R. | 73/54 |

Primary Examiner—Stewart J. Levy
Assistant Examiner—Hezron E. Williams
Attorney, Agent, or Firm—Saul Elbaum; Alan Kennedy; Thomas E. McDonald

[57] ABSTRACT

Presented is a fluid property measuring device which can be used to measure the viscosity, the density, the volumetric flow rate, and the mass flow rate, of a fluid without using moving parts. The fluid property measuring device comprises a linear fluid resistor, a nonlinear resistor, and a linear, fluid property independent, volumetric flowmeter, Two nonlinear resistors, or two linear resistors, may be used instead of a linear and nonlinear resistor. The linear, fluid property independent, volumetric flowmeter comprises a fluidic negative feedback oscillator in fluid connection with a fluidic buffer laminar proportional amplifier.

11 Claims, 8 Drawing Figures

FLUID PROPERTY MEASURING DEVICE

RIGHTS OF THE GOVERNMENT

The invention described herein may be manufactured, used or licensed by or for the Government of the United States of America for governmental purposes without payment to me of any royalties thereon.

BACKGROUND OF THE INVENTION

The purpose of this invention is to present a fluid property measuring instrument which can be used to measure the viscosity, $\mu$, the density, $\rho$, the volumetric flow rate, Q, and the mass flow rate, m, of an unknown fluid. All presently existing volumetric flowmeters are fluid property dependent and require very complicated instrumentation and/or the use of moving parts. The present invention is fluid property independent and uses no moving parts. It does this through the use of fluidics, which is a technology that provides sensing and controlling functions with fluid power through the interaction of fluid streams without using moving parts.

OBJECTS OF THE INVENTION

It is an object of this invention to present a fluid property measuring instrument which can be used to measure the viscosity, $\mu$, the density, $\rho$, the volumetric flow rate, Q, and the mass flow rate, m.

It is another object of this invention to present a fluid property measuring instrument which uses no moving parts.

It is still another object of this invention to present a fluidic flowmeter which is linear and fluid property independent.

Lastly, it is an object of this invention to present a fluidic flowmeter whose output depends only on volumetric flow rate.

SUMMARY OF THE INVENTION

The present invention is a fluid property measuring instrument which can be used to measure the viscosity, the density, the volumetric flow rate, and the mass flow rate of fluids. The fluid whose properties are to be measured are supplied through a pressure regulator to either a linear resistor followed by a nonlinear resistor, a nonlinear resistor followed by a linear resistor, or a first nonlinear resistor followed by a second nonlinear resistor. First and second pressure transducers are placed across the first and second resistors for measuring the pressure drop across each resistor. After the fluid passes through both fluid resistors, it is supplied to a fluidic linear flowmeter.

The fluidic linear flowmeter comprises a fluidic negative feedback oscillator in fluid connection with a fluidic buffer laminar proportional amplifier. The fluidic negative feedback oscillator comprises a laminar proportional amplifier in fluid connection with two feedback resistors. The frequency of oscillation of the fluidic linear flowmeter is linearly related to the fluid flow rate, and it may be determined by the use of a microphone in combination with means to determine the audio frequency of oscillation.

DESCRIPTION OF THE PREFERRED EMBODIMENTS

Figure 1:
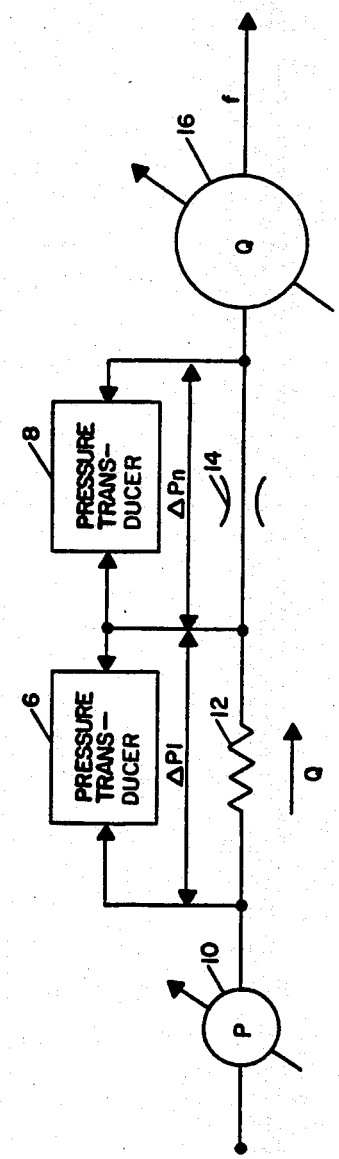
FIG. 1 is a schematic of an embodiment of the fluid property measuring device which employs a linear resistor and a nonlinear resistor.
Figure 2:
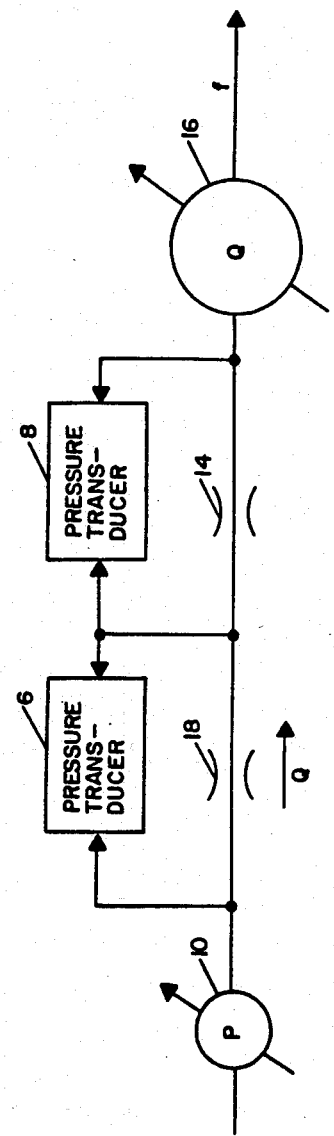
FIG. 2 is a schematic of an embodiment of the fluid property measuring device which employs two nonlinear resistors.

FIG. 1 shows a schematic of the fluidic fluid property meter. It comprises, in series connection, a pressure regulated fluid source 10, a linear resistor 12, a nonlinear resistor 14, and a linear, fluid property independent volumetric flowmeter 16. Pressure transducers 6 and 8 are respectively placed across linear resistor 12 and nonlinear resistor 14. Pressure transducer 6 measures $\Delta P_l$, the pressure drop across the linear resistor 12, and pressure transducer 8 measures $\Delta P_n$, the pressure drop across the nonlinear resistor 14. FIG. 2 shows an alternate embodiment of the fluidic fluid property meter. The only difference between this embodiment and that of FIG. 1 is that nonlinear resistor 18 replaces linear resistor 12. In a third embodiment, not illustrated, a nonlinear resistor replaces linear resistor 12, and a linear resistor replaces nonlinear resistor 14.

The following is a description of the design and operational principles of the embodiment shown in FIG. 1.

It is a known fact that, for a laminar flow, the pressure drop across a linear resistor such as a capillary and a nonlinear resistor such as a nozzle can be respectively written as $$\Delta P_l = R_l \mu Q, \tag{1}$$

and $$\Delta P_n = R_n \mu Q + K_n \rho Q^2 \tag{2}$$

where
$R_l$ = linear resistance coefficient of the linear resistor,
$R_n$ = linear resistance coefficient of the nonlinear resistor,
$K_n$ = nonlinear resistance coefficient of the nonlinear resistor,
$\Delta P_l$ = pressure drop across the linear resistor,
$\Delta P_n$ = pressure drop across the nonlinear resistor,
Q = the volumetric flow rate,
$\rho$ = density,
and
$\mu$ = absolute viscosity.

The constants $K_n$, $R_l$ and $R_n$ are geometric constants which are independent of fluid properties. For a given configuration and size of the resistors, the values of $R_l$, $R_n$, and $K_n$ can be determined experimentally by using a known gas, such a nitrogen, with known viscosity, $\mu$, and density, $\rho$. By least squares fitting of the experimental data, the pressure-flow, P-Q, characteristics can be represented by $$\Delta P_l = R_1 Q, \quad (3)$$

and $$\Delta P_n = R_2 Q + K_2 Q^2, \quad (4)$$

where $R_1$, $R_2$ and $K_2$ are the coefficients of the least squares fitted equations.

By equating the coefficients between equations (1) and (3) and between equations (2) and (4), the geometric constants can be calculated as follows:

$$R_l = R_1/\mu, \quad (5)$$

$$R_n = R_2/\mu, \quad (6)$$

and $$K_n = K_2/\rho, \quad (7)$$

Once, these geometric constants have been determined, the values of $\mu$ and $\rho$ can then be calculated if the values of $\Delta P_l$, $\Delta P_n$ and Q can be measured. However, the flow rate, Q, has to be measured by using a fluid property-independent volumetric flowmeter because the viscosity and density are the unknown parameters which are to be determined. There are many ways to measure the flow rate, Q. One of the most obvious methods is the use of a positive displacement pump or a dead-weight volumetric flow calibrator. Even though these flow measuring devices are property-independent, they are very cumbersome and expensive.

Figure 3:
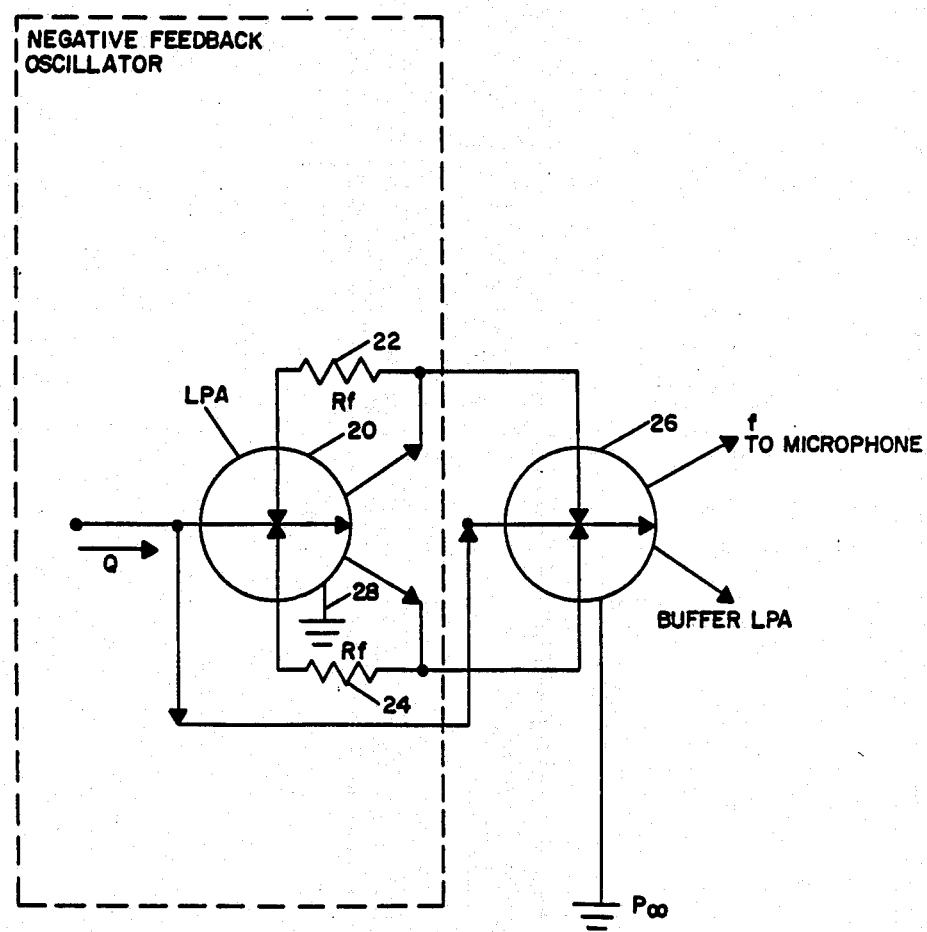
FIG. 3 is a schematic of the fluidic, linear, fluid property independent volumetric flowmeter.

To overcome the disadvantages of the positive displacement pump or the dead-weight volumetric flow calibrator, a fluidic, linear, fluid property independent volumetric flowmeter is presented. FIG. 3 shows a schematic of the flowmeter. It comprises a laminar proportional amplifier (LPA) 20 in fluid connection with a first feedback resistor 22, a second feedback resistor 24, and a buffer laminar proportional amplifier 26. Laminar proportional amplifier 20 contains vent 28. All of the elements, except for the buffer laminar proportional amplifier 26, constitute a negative feedback amplifier. The fluid supply, represented by arrow Q, is supplied to both the laminar proportional amplifier 20 and the buffer laminar proportional amplifier 26. A microphone, not illustrated, is used to measure the frequency of oscillation of the fluidic flowmeter, which is linearly related to the flow rate.

The total period of each oscillation of the flowmeter can be written as $$T = T_j + T_f + T_a \quad (8)$$

These time variables are defined as $$T_a = \frac{2l_f}{a},$$

the acoustic time delay, $$T_f = \frac{2L}{R},$$

the time constant of the feedback channel, and $$T_j = \frac{2X_{sp}}{V},$$

the signal transport time of the supply jet, where $$L = \frac{\rho l_f}{A_f},$$

the inductance of the feedback channel, and $$R = \frac{\rho Q_f}{2A_R^2},$$

the resistance of the feedback channel.

The resistance of the feedback channel is primarily due to the resistance of the area between the edge of the control nozzle and the edge of the supply jet.

In these equations
a = speed of sound,
$A_f$ = area of the feedback channel,
$A_R$ = area between the edge of control nozzle and the edge of the supply jet,
$l_f$ = the length of the feedback channel,
$Q_f$ = the feedback flow rate,
V = the signal transport velocity of the supply jet,
$X_{sp}$ = the distance between the supply nozzle and the splitter,
and
$\rho$ = the fluid density.

In terms of the above parameters, equation (8) can be rewritten as $$T = \frac{2X_{sp}}{V} + \frac{4l_f A_R^2}{A_f Q_f} + \frac{2l_f}{a} \quad (9)$$

The variables V and $Q_f$ can be related to the supply jet flow, $Q_j$, as below:

$$V = \frac{C_1 Q_j}{A_j} \quad (10)$$

$$Q_f = C_2 Q_j \quad (11)$$

where
$C_1$ and $C_2$ = experimentally determined constants.
and
$A_j$ = supply jet nozzle area.

The parameters, $A_j$ and $A_R$ can be written as, $$A_j = h_s b_s = \sigma b_s^2 \quad (12)$$

and $$A_R = C_3 A_j \quad (13)$$

where
$b_s$ = the width of the supply jet nozzle,
$C_3$ = a constant,
$h_s$ = the height of the supply jet nozzle,
and
$\sigma = h_s/b_s$, the aspect ratio.

Substituting equations (10)–(13) into (9), yields $$T = \frac{2}{Q_j}\left(\frac{X_{sp}\sigma b_s^2}{C_1} + \frac{2l(C_3\sigma b_s^2)^2}{C_2 A f}\right) + \frac{2lf}{a} \quad (14)$$

Figure 4:
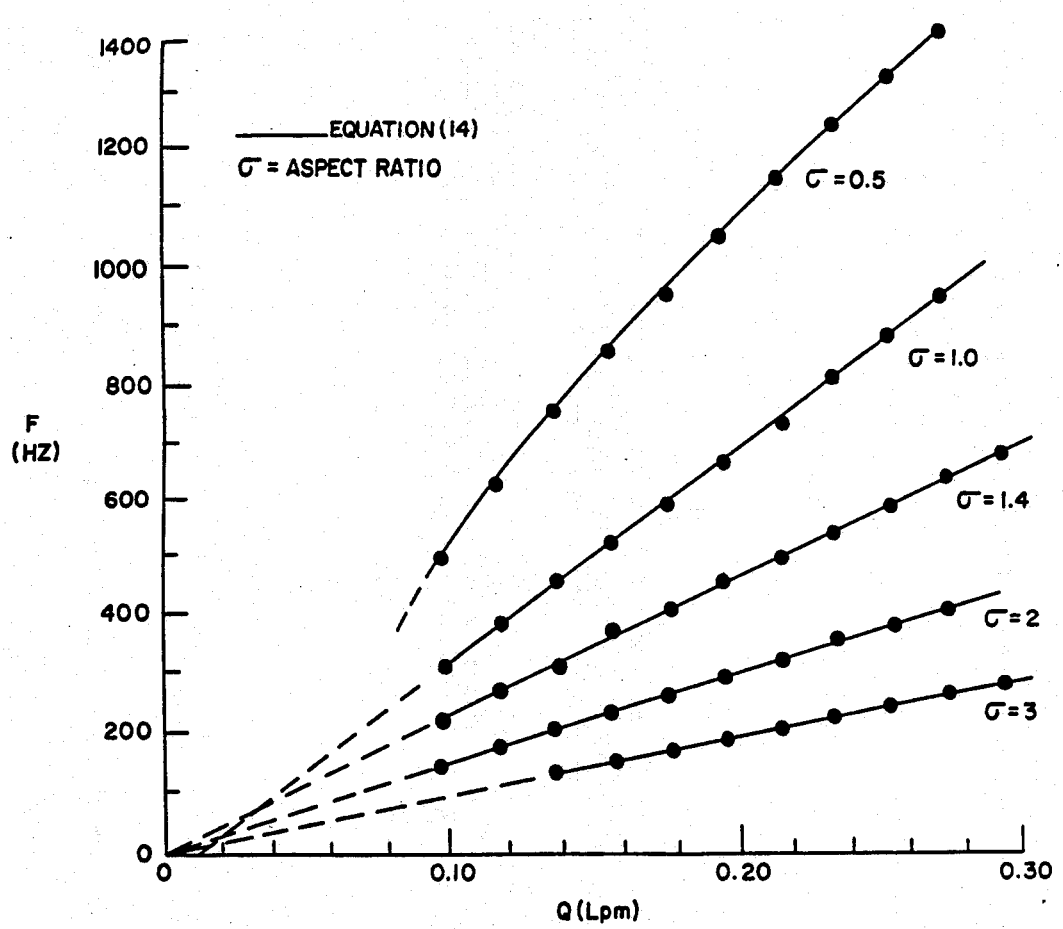
FIG. 4 shows plots of frequency as a function of the flow rate for various values of the aspect ratio.

The above equation indicates that if the first two terms, (the flow dependent terms) can be made much larger than the last term (the acoustic delay term), the frequency, $f=1/T$ would be linearly related to the flow rate, $Q_j$, and independent of the fluid properties. For a given LPA and feedback configuration, the flow dependent terms could be made much larger than the acoustic delay term by increasing the aspect ratio, $\sigma$, of the LPA. FIG. 4 shows plots of the frequency-flow, f-$Q_j$ characteristics of the fluidic flowmeter for various values of the aspect ratio. As predicated by equation (14), a high aspect ratio flowmeter has a linear f-$Q_j$ characteristic.

Figure 5:
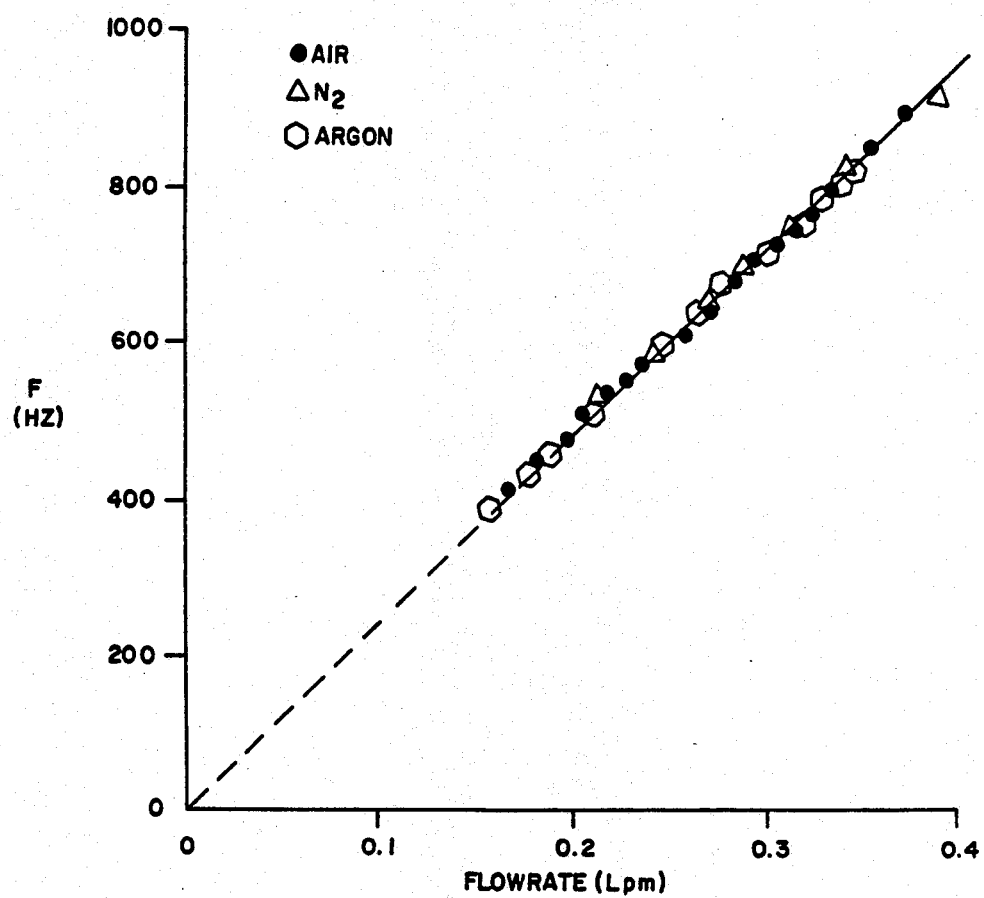
FIG. 5 shows a typical plot of the frequency versus flow rate characteristics of the flowmeter for three different gases.

In order to compare the theoretical predication with the experimental data, the values of the constants $C_1$, $C_2$, and $C_3$ must be determined. For the standard "C" format LPA (the "C" format is a standard format for fluidic elements) with a supply nozzle width, $b_s=0.5$ mm, we have $$C_3 = 0.0625 \quad (15)$$

and with a pressure recovery about 25% the value of $C_2$ is estimated to be 0.03. By using these values for $C_2$ and $C_3$ the value of $C_1$ can, then, be determined by matching the calculated value using equation (14) with the experimental data at a given flow rate, $Q_j$. In this calculation $Q_j=0.2$ LPM was used as the matching point and the values of $C_1 \approx 0.5$ was obtained. This result also shows that a flowmeter with an LPA whose $\sigma$ is greater than 1.4, the f-$Q_j$ characteristic is not only linear but also has no null offset. This is a very desirable feature for any flowmeter. FIG. 5 shows that the f-$Q_j$ characteristic of the flowmeter for three different gases. This f-$Q_j$ characteristic can be represented by a single straight line as given below:

$$Q_j = K_1 f, \quad (16)$$

where $K_1$ is a geometric constant which can be determined experimentally.

Figure 6:
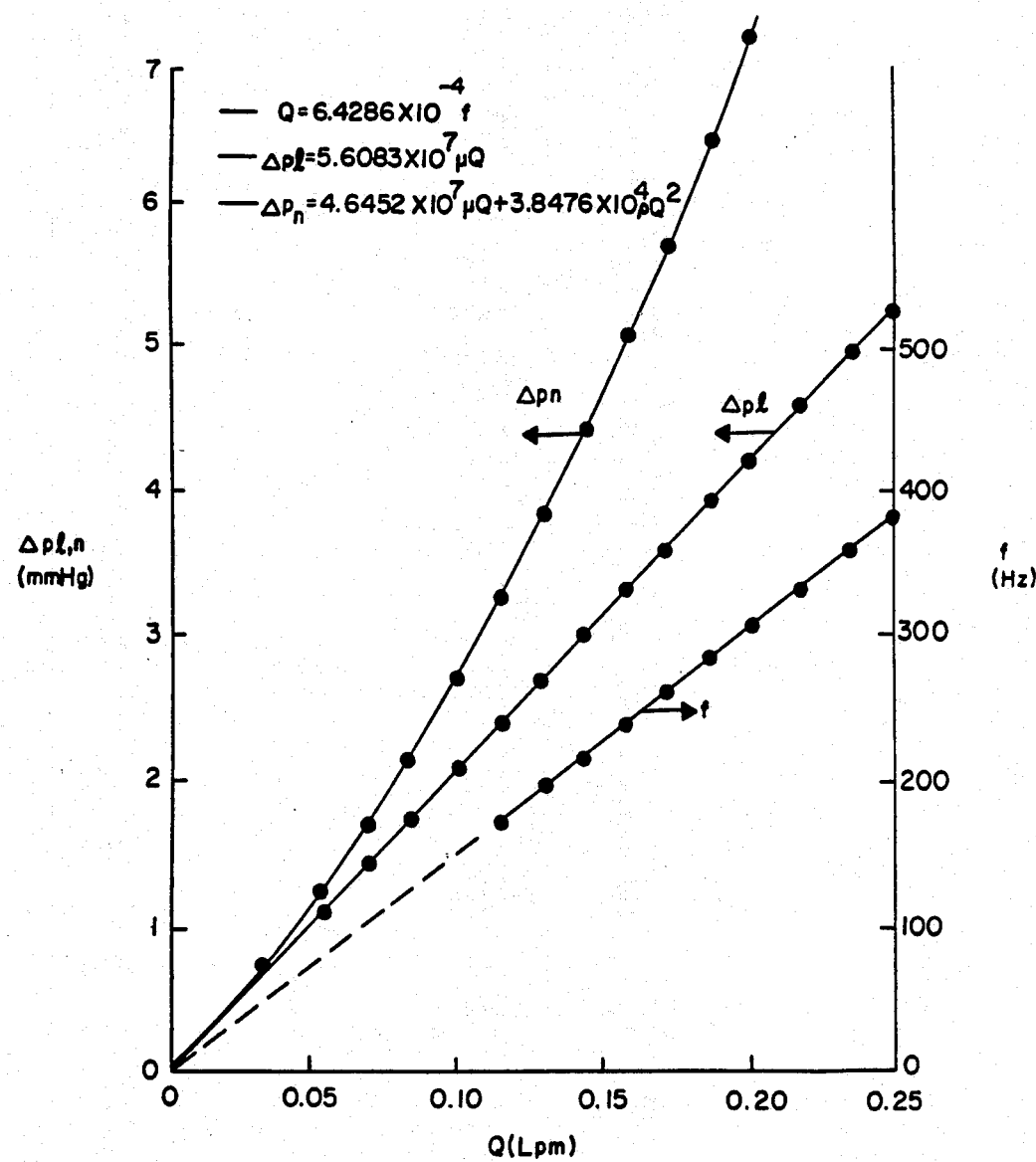
FIG. 6 shows typical plots of the pressure versus flow rate, and frequency versus flow rate characteristics of the flowmeter in combination with the linear resistor and the nonlinear resistor.

FIG. 6 shows typical plots of the performance characteristic of the linear resistor, non-linear resistor and the fluidic flowmeter. This figure also shows the values of the geometric constants, $R_l$, $R_n$, $K_n$, and $K_1$. Once these constants have been determined the values of the viscosity, and density can then be defined in terms of the measured parameters, $\Delta P_l$, $\Delta P_n$ and f by using equations (1), (2), and (16) as follows:

$$\mu = \frac{\Delta P_l}{R_l K_1 f} \quad (17)$$

and $$\rho = \frac{\Delta P_n - \frac{R_n}{R_l}\Delta P_l}{K_n K_1^2 f^2} \quad (18)$$

By knowing $\rho$, the mass flow rate, m, can also be determined as $$m = \rho Q,$$

or $$m = \frac{\Delta P_n - \frac{R_n}{R_l}\Delta P_l}{K_n K_1 f} \quad (19)$$

Equations (17), (18) and (19) are the desired system equations.

Figure 7:
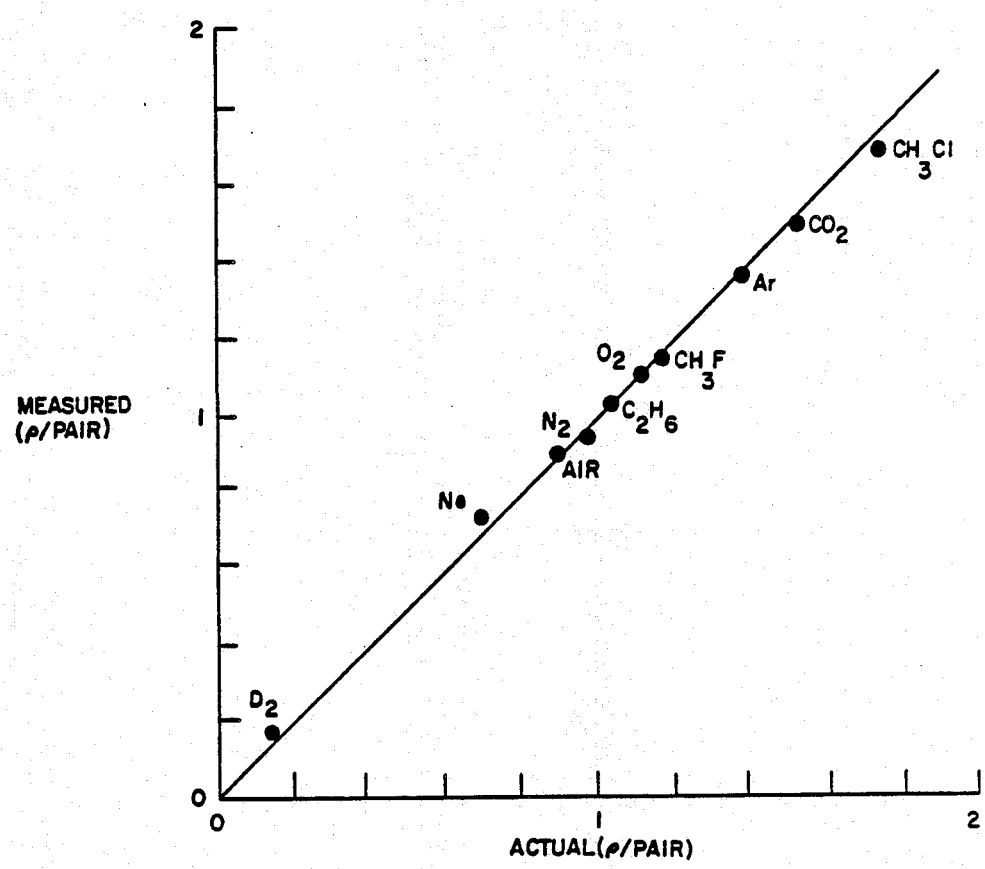
FIG. 7 is a comparison between the measured and actual values of density of various gases.
Figure 8:
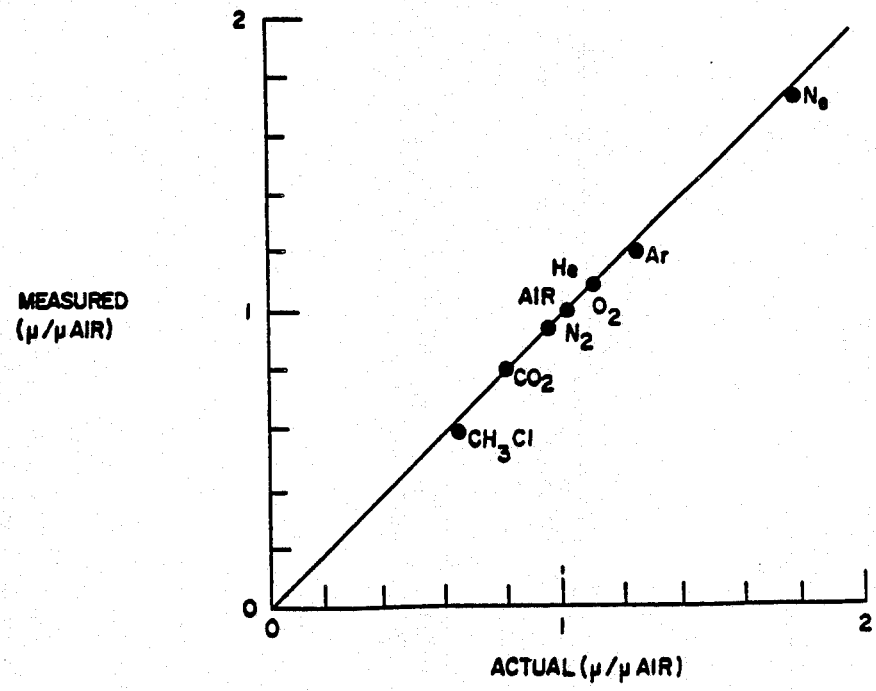
FIG. 8 is a comparison between the measured and actual values of viscosity of various gases.

FIGS. 7 and 8 summarize the test results of the measured values of the density and viscosity for different gases. These figures show that the fluidic meter can indeed measure both density and viscosity without using a reference sample.

If a nonlinear resistor 18 is substituted for linear resistor 12 of FIG. 1, the embodiment shown in FIG. 2 is the result. From FIG. 2, the following equations can be written:

$$\Delta P_1 = R_1\mu Q + K_1\rho Q^2, \quad (20)$$

$$\Delta P_2 = R_2\mu Q + K_2\rho Q^2, \quad (21)$$

and $$Q = A_1 + A_2 f, \quad (22)$$

where
$A_1$, $A_2$ = geometric constants,
$K_1$, $K_2$ = geometric constants,
$R_1$, $R^2$ = geometric constants,
$\Delta P_1$, = differential pressure across the first nonlinear resistor,
$\Delta P_2$ = different pressure from the junction of the two resistors to the oscillator ground, P,
Q = volumetric flow rate,
$\rho$ = density,
and
$\mu$ = viscosity.

From equations (20), (21), and (22), we have $$\mu = \frac{K_2\Delta P_1 - K_1\Delta P_2}{(R_1 K_2 - R_2 K_1)(A_1 + A_2 f)} \quad (23)$$

and $$\rho = \frac{\Delta P_1 - R_1\left(\frac{K_2\Delta P_1 - K_1\Delta P_2}{R_1 K_2 - R_2 K_1}\right)}{K_2(A_1 + A_2 f)^2} \quad (24)$$

By knowing $\rho$, the mass flow rate, M, can also be determined as $$\dot{M} = \rho(A_1 + A_2 f) \quad (25)$$

Equations (23), (24), and (25) are the system equations.

It is probably advantageous to use the second embodiment of this invention where the two nonlinear resistors in series are used as sensing elements, because it is much easier to construct a nonlinear resistor than a linear resistor. This is because linear resistors still have a nonlinear component, and for comparable pressure-flow characteristics, the flow passage of a linear resistor is much smaller than that of a nonlinear resistor.

Both embodiments of the invention can be constructed out of off-the-shelf "C" format fluidic active and passive components. The "C" format fluidic laminates can be stacked to form different fluidic systems without using interconnecting tubing. All of the fluidic components may be enclosed in a single enclosure.

While the invention has been described with reference to the accompanying drawings, I do not wish to be limited to the details shown therein as obvious modifications may be made by one of ordinary skill in the art.

What is claimed is:

1. A device for measuring viscosity, density, volumetric flow rate, and mass flow rate of a gas or liquid comprising:
   a. a laminar flow fluid source;
   b. a first fluid resistor in fluid connection with said fluid source;
   c. a second fluid resistor in fluid connection with said first fluid resistor;
   d. a first pressure transducer to measure the pressure drop across said first fluid resistor;
   e. a second pressure transducer to measure the pressure drop across said said fluid resistor; and
   f. a fluidic linear flowmeter in fluid connection with said second fluid resistor.

2. The device of claim 1 wherein said fluidic linear flowmeter comprises:
   a. a negative feedback oscillator; and
   b. a buffer laminar proportional amplifier.

3. The device of claim 2 wherein said negative feedback oscillator comprises:
   a. a laminar proportional amplifier;
   b. a first feedback resistor; and
   c. a second feedback resistor.

4. The device of claim 1, wherein said first and second fluid resistors respectively comprise a linear and a nonlinear resistor.

5. The device of claim 1 wherein said first and second fluid resistors are both non-linear resistors.

6. The device of claim 1 wherein said first and second fluid resistors respectively comprise a nonlinear and a linear resistor.

7. A device for measuring viscosity, density, volumetric flow rate, and mass flow rate of a gas or liquid comprising:
   a laminar flow fluid source;
   a first fluid resistor in fluid connection with said fluid source;
   a second fluid resistor in fluid connection with said first fluid resistor;
   a first pressure transducer to measure the pressure drop across said first fluid resistor;
   a second pressure transducer to measure the pressure drop across said second fluid resistor;
   a negative feedback oscillator in fluid connection with said second fluid resistor, said negative feedback oscillator comprising a laminar proportional amplifier, a first feedback resistor, and a second feedback resistor; and
   a buffer laminar proportional amplifier in fluid connection with said negative feedback oscillator.

8. The device of claim 7, wherein said first and second fluid resistors respectively comprise a linear and a nonlinear resistor.

9. The device of claim 7 wherein said first and second fluid resistor are both non-linear resistors.

10. The device of claim 7 wherein said first and second fluid resistors respectively comprise a nonlinear and a linear resistor.

11. The device of claim 7 further comprising means for measuring the frequency of oscillation of said negative feedback oscillator.

* * * * *